United States Patent
Mora et al.

(10) Patent No.: US 6,891,063 B1
(45) Date of Patent: May 10, 2005

(54) SALTS OF ASIATIC AND MADECASSIC ACID SUITABLE FOR THE PREPARATION OF PHARMACEUTICAL AND COSMETIC COMPOSITIONS

(75) Inventors: Paolo Corvi Mora, Piacenza (IT); Angelo Ranise, Genoa (IT)

(73) Assignee: Euphar Group S.r.l., Milan (IT)

( * ) Notice: Subject to any disclaimer, the term of this patent is extended or adjusted under 35 U.S.C. 154(b) by 0 days.

(21) Appl. No.: 10/018,259

(22) PCT Filed: Apr. 19, 2000

(86) PCT No.: PCT/EP00/03551
§ 371 (c)(1),
(2), (4) Date: Oct. 22, 2001

(87) PCT Pub. No.: WO00/63148
PCT Pub. Date: Oct. 26, 2000

(30) Foreign Application Priority Data

Apr. 21, 1999 (IT) .......................... MI99A0835

(51) Int. Cl.[7] .......................... C07C 61/12; A61K 9/70; A61K 13/00; C09B 3/50
(52) U.S. Cl. ...................... 562/498; 424/400; 424/401; 424/443; 552/284
(58) Field of Search ................ 424/400, 401, 424/443; 552/284; 562/498; 514/944

(56) References Cited

U.S. PATENT DOCUMENTS 3,366,669 A * 1/1968 Ratsimamanga ............ 560/194

4,393,048 A * 7/1983 Mason et al. ............... 424/619

FOREIGN PATENT DOCUMENTS

WO    WO98/23574    6/1998

OTHER PUBLICATIONS

F. Bonte et al. *Influence of Asiatic Acid, Madecassic Acid, and Asiaticoside on Human Collagen I Synthesis*. Planta. Med. vol. 60, 1994, pp. 133–135.

Francois–Xavier Maquart et al. *Stimulation of Collagen Synthesis in Fibroblast Cultures by a Triterpene Extracted From Centella asiatica*. Connective Tissue Research, vol. 24, 1990, pp. 107–120.

Pil–Jong Shim et al. *Asiaticoside Mimetics As Wound Healing Agent*. Bioorganic & Medicinal Chemistry Letters, vol. 6, No. 24, 1996, pp. 2937–2940.

* cited by examiner

Primary Examiner—Thurman K. Page
Assistant Examiner—Sharon Howard
(74) Attorney, Agent, or Firm—Morgan & Finnegan, L.L.P.

(57) ABSTRACT

Salts of asiatic and madecassic acid with pharmaceutically acceptable organic bases, suitable for the preparation of pharmaceutical and cosmetic compositions for the topical and systemic treatment of erithema, varicose ulcers, venous insufficiency, bedsores, delayed cicatrization, ambustions, traumatic and surgery wounds, alloeosises of the cutaneous trophism, ophthalmic alloeosises and inflammatory processes.

8 Claims, 1 Drawing Sheet

Dose-activity relationship for Asialene and L-Asialene

SALTS OF ASIATIC AND MADECASSIC ACID SUITABLE FOR THE PREPARATION OF PHARMACEUTICAL AND COSMETIC COMPOSITIONS

FIELD OF THE INVENTION

The present invention relates to the preparation of salts of asiatic and madecassic acid suitable for the preparation of pharmaceutical and cosmetic compositions.

PRIOR ART

Asiatic ($2\alpha$, $3\beta$, 23-trihydroxyurs-12-en-28-oic acid) acid (1), madecassic acid (2) and asiaticoside (3) represent the main constituents of the triterpemic total fraction (FTT) of the Centella Asiatica.

Digestive, diuretic, reconstituent, cooling, tonic, antipyretic and cicatrizing properties were recognized to said FTT. However the pharmacological interest was mainly focused on the last activity.

In fact it was demonstrated that the FTT of the Centella Asiatica is provided with a peculiar modulating activity on the connective tissue, through an action on the fibroblasts and on two aminoacids fundamental for the metabolism of the collagen: proline and alanine.

All this results in a higher biostimulation of the wound healing processes and in a better reepithelialization.

Therefore, the therapeutic use of FTT of the Centella is tergeted to the treatment of erithema, varicose ulcers, bedsores, delayed cicatrization, ambustions, traumatic and surgery wounds, systemic and topical inflammatory processes. The literature data are concordant to consider that the asiatic acid is the most active component of the FTT of the Centella Asiatica in the stimulation of the fibroblasts and consequently in helping the reepithelialization phenomena (F. Bonte, M. Dumas, C. Chaudagne, A. Meybeck. Planta Med. 60, 133, 1994. F. X. Maquart, G. Bellon, P. Gillery, Y. Wegrowski, J. Borcel, Connet Tissue Res. 24, 107, 1990) which however presents considerable problems in the preparation of compositions suitable to topic treatment. Similar problems are encountered with madecassic acid.

In fact, in spite of the presence in their molecular structure of 4 hydrophilic functions (4 hydroxylic groups wherein 3 groups are alcoholic and one is acid), both asiatic and madecassic acid show a poor wettability and an almost total

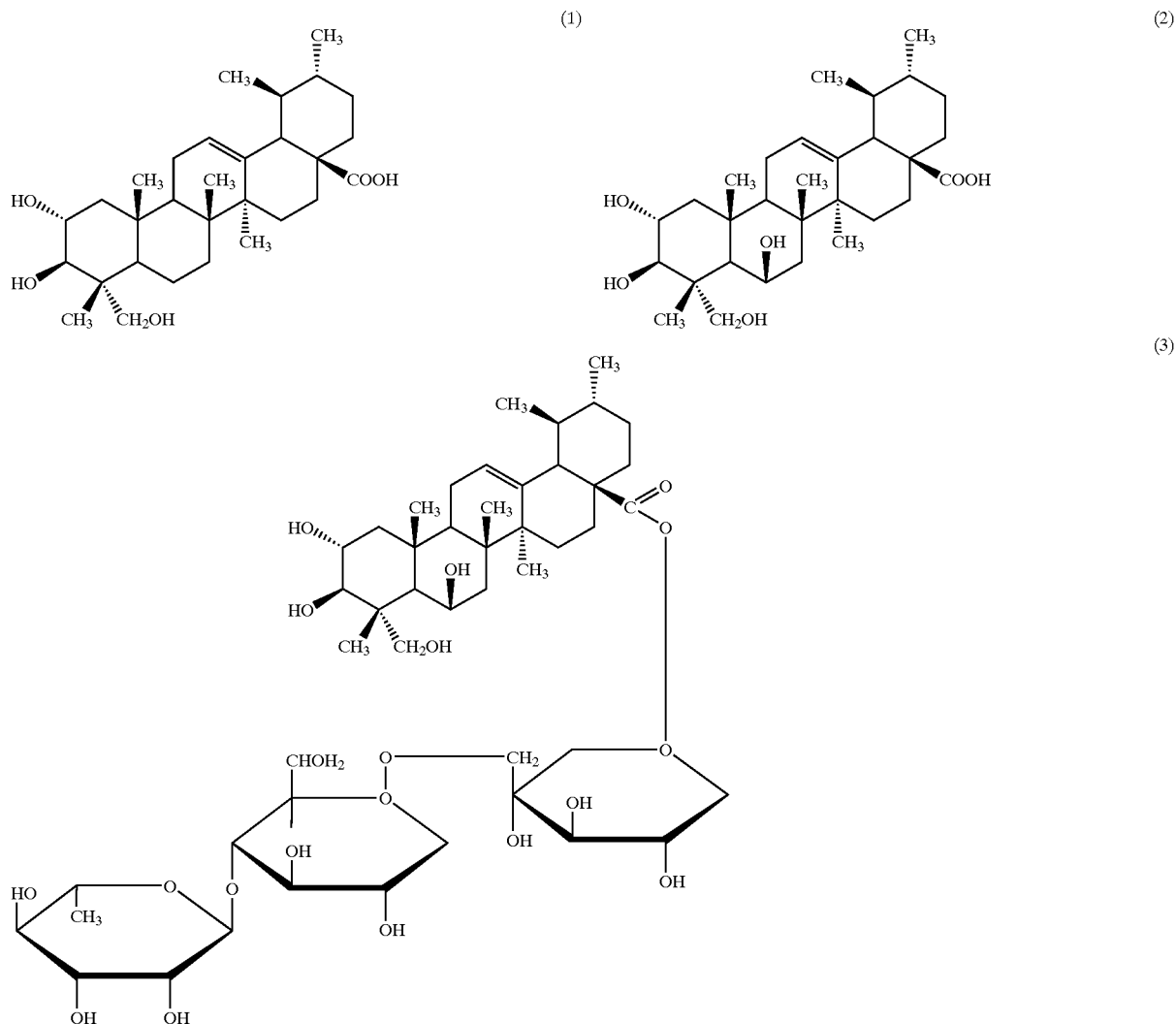

insolubility in water, physicochemical characteristics which require particular techniques of preparation and particular excipients in the formulation of preparations for topic use, particularly of hydrophilic kind. Furthermore, it is known that the cutaneous absorption mainly happens by transepidermic way (intra- and trans-cellular) and it is mainly controlled by the behaviour of the active principle towards the corneum, mainly formed by keratin and water.

Therefore, in addition to the formulative problems also the problems of a suitable bioavailability of asiatic and madecassic acid at the dermis level remain open (P.-J. Shim, J.-H. Park, M.-Sun Chang, M.-J. Lim, D. Kim, Y. H. Yung, S.-S. Jew, E. H. Pavk, H.-Doo Kim, Bio Organic and Medical Chemistry Letters 24, 2937, 1996). Organic salts and derivatives of asiatc acid have been disclosed. For example U.S. Pat. No. 3,366,669 discloses hemisuccinates and salts of hemisuccinates of asiatic acid and salts of alkylaminoalkanols and dialkylaminoalkanols of asiatic acid. Said compounds permit the preparation of aqueous solutions for local uses in therapeutics.

WO98/23574 discloses derivatives of asiatic acid wherein the carboxylic group may be combined with an alkyl group having 1 to 4 carbon atoms, an alkoxymethyl group having 1 to 4 carbon atoms, octyloxymethyl, methoxyethoxymethyl, benzyloxymethyl or 2-tetrahydropiranyl group.

Also a medicine for treating would which comprises said derivatives is disclosed.

SUMMARY OF THE INVENTION

Figure 1:
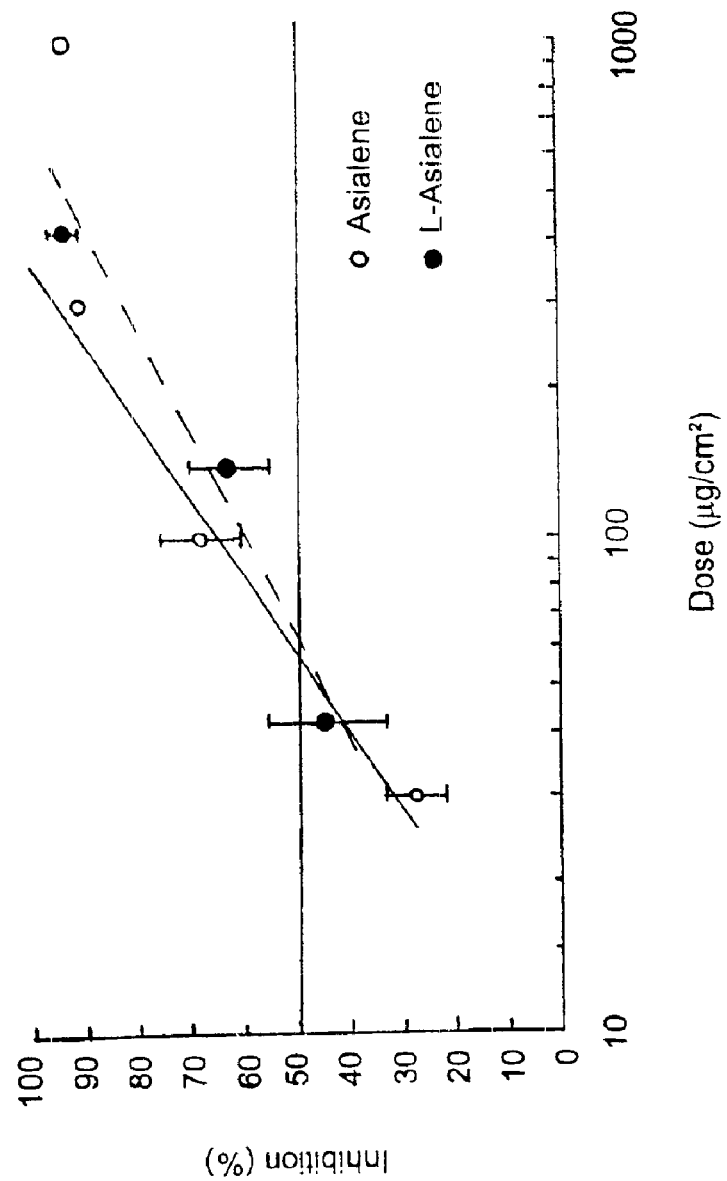
FIG. 1 shows the percentage of inhibition of the oedema observed with different doses of Asialene (a) and L-Asialene (b).

Now it was found that the problems of the Prior Art may be solved by the salts of the acids of the triterpenic fraction of the Centella Asiatica as, for example, salts of asiatic and madecassic acid with pharmaceutically acceptable organic bases according to the present invention.

In fact, said salts allow:
a) to prepare easily hydrophilic gels which facilitate the formulation of compositions for topic use;
b) to increase the topic bioavailability of asiatic and madecassic acid at the dermis level; and moreover they are also suitable for the preparation of pharmaceutical compositions for systemic treatment.

These and other characteristics of the salts of asiatic and madecassic acid according to the present invention will be mainly illustrated during the following detailed description.

DETAILED DESCRIPTION OF THE INVENTION

The present invention refers to salts of asiatic and madecassic acid with pharmaceutically acceptable organic bases, suitable for the preparation of pharmaceutical and cosmetic compositions.

Said bases include ethylenediamine, ethanolamine, diethanolamine, lysine, benzyltrimethylammonium hydroxide and tetramethylammonium hydroxide.

The preparation of said salts is carried out according to the following steps:
a) a solution of the organic base is prepared in an organic solvent as for example chloroform or ethanol, at room temperature;
b) a solution of asiatic or madecassic acid is prepared in an organic solvent as for example methanol, heating at a temperature ranging from 60 to 80° C.;
c) the solution of asiatic or madecassic acid is slowly added to the solution of the organic base, under stirring at room temperature;
d) the mixture obtained in the step c) is heated at a temperature ranging from 60 to 70° C. for a time ranging from 10 to 30 minutes;
e) the solvent is removed under vacuum at a temperature ranging from 55 to 60° C.;
f) the obtained residue is washed with an organic solvent and then it is crystallized by a suitable organic solvent.

The molar ratio between the organic base and the asiatic or madecassic acid, used in the reaction, ranges from 3:1 to 1:1.

The obtained salts were characterized, besides with the usual analytical methods, as will be reported in the examples, also by infrared spectrophotometry using a PERKIN ELMER 398 spectrophotometer.

The IR (K Br) spectra of the prepared salts show the presence of quite intense bands at about 1540 and 1380 $cm_{-1}$ attributable respectively to the antisymmetric and symmetric stirring frequencies of the carboxylated group, as a spectroscopic proof of occured salification.

Moreover, a very intense band formed by ammonic and alcoholic bands is observed between 3600 and 3100 $cm_{-1}$. Also some overtones or combination bands in the zone between 2500 and 2000 $cm_{-1}$ caused by primary ammonic groups are present in the spectra of the salts 4, 5a, 5c, 7 and 8a described in the examples.

The salts according to the invention, when they are treated with water at a ratio by weight between salt and water ranging from 1:12 to 1:20 are able to assume the form of a gel. This property facilitates the preparation of the compositions for topic use with hydrophilic gel.

Moreover said salts allow a modulation of the hydrophilic-lipophylic balance by a suitable choice of the organic base which may exhibit (hydoxylic or α-aminoacids) polar groups or (tetramethyl or benzyltrimethyl) apolar substituents.

The salts according to the present invention have antiinflammatory and cicatrizing effects unexpectedly higher than the total triterpenic fraction (FTT) of the Centella Asiatica and therefore they can be successfully used in the preparation of pharmaceutical and cosmetic compositions for topic treatment of erithema, varicose ulcers, venous insufficiency, bedsores, dalayed cicatrization, ambustions, traumatic and surgery wounds, ophthalmic and cutaneous trophism alloeosises and inflammatory diseases. Moreover, said salts may be used for the preparation of compositions for systemic use, oral and parenteral, with the same therapeutcal and cosmetic aims.

Said compositions contain a pharmaceutically effective or cosmetically suitable amount of a salt of the present invention in mixture with pharmaceutically acceptable or cosmetically suitable excipient and/or diluent substances.

The following Examples are reported for illustrative aim of the invention:

EXAMPLE 1

Preparation of the Salt of the Asiatic Acid with Ethylenediamine (4)

This preparation is carried out according to the following reaction:

$$2HAs + H_2N-CH_2CH_2-NH_2 \rightarrow As\ H_3N-CH_2CH_2-NH_3\ As \quad (4)$$

wherein the asiatic acid is indicated with HAs. This abbreviation will be also used in the following examples with the same meaning.

A methanolic solution (50 ml) of asiatic acid (4.89 g, 10 mmol) dissolved at a temperature equal to 60° C. is added to a chloroformic solution (30 ml) of ethylenediamine (1.80 g, 30 mmol) at room temperature under stirring and drop by drop.

When the addition is finished, the mixture is heated at 60–65° C. for 20 minutes. After the removal of the solvents under vacuum, the viscous residue is washed 2 times with ether (30 ml×2), one time with acetonitrile (30 ml) and finally it is hot crystallized with ethanol (95%). An amorphous white solid is obtained, which crystallizes with two molecules of water. M.p. 311–317° C.

$C_{62}H_{108}N_2O_{12}$ Calculated: C: 69.37; H: 10.14; N: 2.61
Found: C: 69.16; H: 10.10; N: 2.59

The melting point was determined with a Fisher-John apparatus and the elementary analyses were executed with an EA 1110 elementary analyzer of the FISON INSTRUMENTS S.p.A. society (Milan).

EXAMPLE 2

Preparation of the Salts of the Asiatic Acid Respectively with Ethanolamine (5a), with Diethanolamine (5b) and with Lysine (5c)

This preparation is carried out according to the following reaction:

$$HAs + HN\begin{matrix}R_1\\R_2\end{matrix} \longrightarrow As^-H_2N^+\begin{matrix}R_1\\R_2\end{matrix}$$

5a–c

5a: $R_1$ = H, $R_2$ = $CH_2CH_2OH$
5b: $R_1$ = $R_2$ = $CH_2CH_2OH$
5c: $R_1$ = H, $R_2$ = $(CH_2)_4$—CH—COOH
                                    |
                                    $NH_2$

A methanolic solution (80 ml) of asiatic acid (4.89 g, 10 mmol) is added at room temperature under stirring to a solution in methanol (80 ml) of the organic base (12 mmol), ethanolamine, diethanolamine and lysine, respectively.

After 15 minutes from the addition, the mixture is heated at 50–60° C. for 20 minutes.

The methanol is removed by vacuum evaporation and the obtained residues are crystallized using suitable solvents, in particular the compounds 5a and 5b are crystallized by methanol-acetone mixtures and the compound 5c by methanol.

The melting points of the three prepared compounds are the following:
5a: 241–245° C.;
5b: 299–305° C.;
5c: 300–314° C.

The elementary analyses of the three prepared compounds give the following results:
5a: $C_{32}H_{59}NO_8$ Calculated: C: 65.61; H: 10.15; N: 2.39
Found: C: 65.41; H: 10.07; N: 2.45
5b: $C_{34}H_{63}NO_9$ Calculated: C: 64.83; H: 10.08; N: 2.22
Found: C: 64.95; H: 9.98; N: 2.30
5c: $C_{36}H_{66}N_2O_9$ Calculated: C: 64.45; H: 9.92; N: 4.18
Found: C: 64.65; H: 9.99; N: 4.07

EXAMPLE 3

Preparation of the Salts of the Asiatic Acid with Tetramethylammonium (6a) and with Benzyltrimethylammonium (6b) Hydroxides This preparation is carried out according to the following reaction:

$$HAs + (CH_3)_3—\overset{R_3}{\underset{R_3}{N^+}}OH^- \longrightarrow As^-\overset{R_3}{\underset{R_3}{N(CH_3)_3^+}} + H_2O$$

6 a–b

6a: $R_3$ = $CH_3$
6b: R = $C_6H_5CH_2$

A methanolic solution (80 ml) of asiatic acid (4.89 g, 10 mmol) is added at room temperature under stirring to a solution in methanol (80 ml) respectively of tetramethylammonium hydroxide and of benzyltrimethylammonium hydroxide (12 mmol).

After 15 minutes the mixture is heated at 50–60° C. for 20 minutes.

The residues obtained after vacuum removal of the methanol are crystallized by suitable solvents, in particular the compound 6a is crystallized by a methanol-acetone mixture and the compound 6b by a methanol-acetonitrile mixture.

The melting points of the two prepared compounds are the following ones:
6a: 214–220° C.;
6b: 203–209° C.

The elementary analyses of the two prepared compounds give the following results:
6a: $C_{34}H_{63}NO_7$ Calculated: C: 68.30; H: 10.62; N: 2.34
Found: C: 68.12; H: 10.43; N: 2.38
6b: $C_{40}H_{67}NO_7$ Calculated: C: 71.28; H: 10.02; N: 2.08
Found: C: 71.54; H: 10.21; N: 1.98

EXAMPLE 4

Preparation of the Salt of Madecassic Acid with Ethylendiamine (7)

This preparation is carried out according to the following reaction:

$$HMAD + H_2N—CH_2CH_2—NH_2 \rightarrow MAD\ H_3N^+—CH_2CH_2—NH_2 \quad (7)$$

Wherein the madecassic acid is indicated with HMAD. This abbreviation will be also used in the following examples.

The same procedure as that decribed in example 1 is carried out using, instead of asiatic acid, a methanolic solution (50 ml) of madecassic acid (5.05 g, 10 mmol).

The salt crystallizes with one molecule of water. M.p. 170–178° C.

The elementary analysis of the obtained compound gives the following result:
$C_{32}H_{58}N_2O_7$ Calculated: C: 65.95; H: 10.03; N: 4.81
Found: C: 65.66; H: 9.78; N: 4.74

EXAMPLE 5

Preparation of the Salt of Madecassic Acid with Ethanolamine (8a) and with Diethanolamine (8b)

This preparation is carried out according to the following reaction:

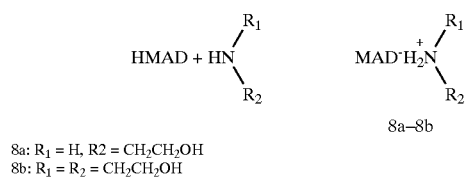

8a: R₁ = H, R₂ = CH₂CH₂OH
8b: R₁ = R₂ = CH₂CH₂OH

The same procedure as that decribed in example 2 is carried out using, instead of asiatic acid, a methanolic solution (80 ml) of madecassic acid (5.05 g, 10 mmol). Crystallization is performed in methanol-acetone.

The elementary analyses of the two prepared compounds confirm the following formulas:
8a: $C_{32}H_{58}NO_8$
88: $C_{36}H_{61}NO_9$

EXAMPLE 6

Preparation of the Salt of Madecassic Acid with Tetramethylammonium (9a) and With Benzyltrimethylammonium (9b) Hydroxides This preparation is carried out according to the following reaction:

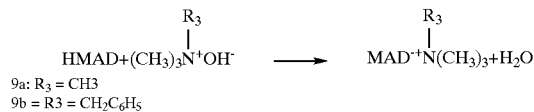

9a: R₃ = CH3
9b = R3 = CH₂C₆H₅

The same procedure as that decribed in example 3 is carried out using, instead of asiatic acid, a methanolic solution (80 ml) of madecassic acid (5.059, 10 mmol). 9a is crystallized in a methanol-acetone mixture and 9b in a ethanol-acetonitrile mixture.

The elementary analyses for the two compounds confirm the following formulas:
9a: $C_{34}H_{61}NO_7$
9b: $C_{41}H_{65}NO_7$

EXAMPLE 7

Preparation of the Gel of the Salt of the Asiatic Acid with Ethylenediamine 1 g of the salt of the asiatic acid with ethylenediamine, salt (4), prepared as described in the Example 1, is loaded in a flask equipped with a magnetic stirrer. 15 ml of water are then added at room temperature and stirring is begun at a low revolution number (100–150 revolutions per minute).

The water is gradually included in the salt in order to form a gel while the stirring revolution number is gradually increased to 1000–1500 revolutions per minute.

A gel having semisolid consistency is formed in a time equal to 4–6 minutes, which becomes translucent continuing the stirring for 5–8 minutes.

Biological Tests

In order to verify the cicatrizing and platelet antiaggregation activity of the salts of the present invention in comparison with the products of the prior art, tests reporting the comparison between the salt prepared in Example 1, indicated as Asialene and the total triterpenic fraction of the Centella Asiatica, indicated as FTT, were carried out.

Furthermore, the antiinflammatory activity of Asialene and L-Asialene, the salt of asiatic acid with lysine prepared in Example 2, was evaluated in comparison with that of NSAID indomethacin.

1. Test of Production of PG1 and of Fibronectin from Human Endothelial Cells in Culture.

The activity of the salt prepared in the Example 1, indicated as Asialene, on cicatrization was evaluated by an in vitro test which allows to deduce the effects of the substance on the vascular permeability and on the cicatrization.

The test consists in the evaluation of the production of PG1 from cells extracted by collagenase from vein of human omphalic funicle suspended and seeded in a suitable culture medium (E199+FCS 20%+L-Glutamine 2 mM+Penicillin 200 U/ml+Streptomycin 200 μg/ml) cultured in 75 or 25 ml flasks for 48–72 hours.

After removing the cells with 0.05% Trypsin and 0.02% EDTA the subcultures were prepared using secondary cultures seeded on a 35 mm Petri dish, kept in an incubator with 5% $CO_2$ and 100% humidity. For the evaluation of the cell morphology and confluence and the PG1 production, about 300,000 cells/ml of culture medium were used carrying out the count in a Burker chamber, following three schemes:
1. Cells+culture medium+EtOH(0.75 g/dl)
2. Cells+culture medium+EtOH(0.75 g/dl)+FTT(151 g/ml)
3. Cells+culture medium+EtOH(0.75 g/dl)+Asialene(1.5 μg/ml)

The cultures were evaluated with an inverse light microscope, at 24 and 48 hours monitoring cell attachment and growth while on supernatant aliquots the stable metabolite of the prostacyclin (6-Keto PGF1) was assayed with RIA method.

In the following table the values of 6-Keto PGF1 in μg/ml are reported. (The cicatrizing activity is correlated to the 6-Keto PGF1 levels).

|  | 24 h | 48 h |
| --- | --- | --- |
| Culture medium + EtOH (0.75 g/dl) | 415 | 380 |
| Culture medium + EtOH (0.75 g/dl) + FTT (15 μg/ml) | 520 | 475 |
| Culture medium + EtOH (0.75 g/dl) + Asialene (1.5 μg/ml) | 980 | 889 |

For the Fibronectin evaluation, the primary cultures were resuspended in 0.05% Trypsin/0.02% EDTA. The cells, washed twice in Hanks solution, were counted in order to assure at least 300,000 cells/ml and seeded. After 48 hours the supernatant was removed and the slides were prepared, which after being washed 2 times with PBS, and dried, were fixed in acetic acid/ethanol for 30 minutes; a washing with PBS was then carried out and added the polyclonal rabbit anti-human fibronectin antibody (1:40, Dako). After incubation at room temperature for 30 minutes, it was washed with PBS and the fluoresceinated anti-rabbit immunoglobulin antibody was added (1:100, Dako). The slides were left in incubation for 30 minutes and then mounted on an object holder and read with a fluorescence electronic microscope.

In the following table, the numbers relating to fibronectin intercellular strands (1:100 scale) are reported.

| | |
|---|---|
| Culture medium + EtOH (0.75 g/dl) | 1 |
| Culture medium + EtOH (0.75 g/dl) + FTT (15 µg/ml) | 7 |
| Culture medium + EtOH (0.75 g/dl) Asialene (1.5 µg/ml) | 85 |

2. Evaluation of the Platelet Aggregation Inhibiting Effect

Blood taken from healthy volunteers not submitted to pharmacological therapy during one week, was gathered in polyethylene test-tubes containing 3.8% sodium citrate in 1:9 ratio, and centrifuged at 1000 g for 10 minutes in order to obtain plasma having a high platelet content (PRP) and at 3000 g for 15 minutes in order to obtain plasma having a low platelet content (PPP). Two 40011 PRP samples (300,000+/−10000 platelet/ml final concentration) were submitted to incubation at 37° C. for 60 seconds in presence of 100 µl FTT (700 µg/ml) and 10 µl of Asialene (701 g/ml) respectively. Each sample was divided in three portions which were treated with 10 µl of a platelet aggregation agent, ADP (4 mM final concentration), collagen (4 µg/ml final concentration) and arachidonic acid (0.2 mg/ml final concentration) respectively, and the aggregation was recorded for 4 minutes.

The obtained results are reported in the following table.

| | CONTROLS | FTT 700 µg/ml | ASIALENE 70 µg/ml |
|---|---|---|---|
| Aggregation from collagen (4 µg/ml) | 100 | 70 | 50 |
| Aggregation from ADP (4 mM) | 88 | 45 | 32 |
| Aggregation from arachidonic acid (0.2 mg/ml) | 81 | 31 | 23 |

3. Test of Topical Antiinflammatory Activity

The antiinflammatory activity of Asialene and L-Asialene was evaluated in comparison to that of the NSAID indomethacin. As experimental model, the Croton oil dermatitis induced in the mouse ear was used (Tubaro et al., Agents & Actions 17: 347–349).

The experimental inflammation was induced on the right ear (surface: about 1 cm$^2$) of anaesthetised mice (145 mg/kg ketamine hydrochloride i.p.) by application of 80 µg of Croton oil (Sigma-Italy) in 15 µl acetone on the right ear of mice, the left remaining untreated. The tested substances were dissolved in the Croton oil solution. Six hours after the dermatitis induction, the animals were sacrificed and a punch (6 mm diameter) was excised from both the treated and the untreated ears and weighed. The Croton oil induced oedema was quantified by measuring the difference in weight between the treated and untreated (opposite) ear samples. The anti-oedema activity was expressed as percent inhibition of the oedematous response in animals treated with the test substances in comparison to the animals treated with the irritant alone. Male albino Swiss mice CD-1 (Harlan-Italy), weighing 20–32 g, were used. For each substance and dose level, 10 animals were used.

The effects on the vascular response were evaluated as percent oedema inhibition. Results were analysed by means of the Student's "t" test, accepting as significant a value of p inferior to 0.05. For each substance, the dose level able to reduce by 50% the oedematous response ($ID_{50}$) was calculated by linear interpolation from the dose-response relationship.

Asialene and L-Asialene were administered at equimolar doses. The obtained results are reported in the following table.

| Substance | Dose (µg/cm$^2$) | Oedema (mg) m ± E.S. | Inhibition (%) |
|---|---|---|---|
| Asialene | 0 | 6.9 ± 0.2 | — |
| | 30 | 5.0 ± 0.4* | 27.5 |
| | 100 | 2.2 ± 0.5* | 68.1 |
| | 300 | 0.6 ± 0.1* | 91.3 |
| | 1000 | 0.4 ± 0.1* | 94.2 |
| L-Asialene | 0 | 7.0 ± 0.4 | — |
| | 42 | 3.9 ± 0.7* | 44.6 |
| | 141 | 2.6 ± 0.5* | 63.5 |
| | 423 | 0.4 ± 0.2* | 94.5 |
| Indomethacin | 90 | 3.5 ± 0.4* | 49.3 |

*0.05 at the Student's "t" test

The two products show a strong inhibition of the oedema induced by Croton oil, in a dose-depending way. At the lowest dose tested (30 µg/cm$^2$), Asialene provokes a significant oedema inhibition that reaches almost the maximum at 300 µg/cm$^2$. As shown in FIG. 1, the dose-activity relationship for Asialene represents the higher branch of the classical sigmoid and is linear in the range from 30 to 300 µg/cm$^2$, whereas at 1000 µg/cm$^2$, the activity lies on the asymptotic part of the curve. From the linear part, an $ID_{50}$ value of 62 µg/cm$^2$ can be calculated. L-Asialene shows a practically superimposable effect from which an $ID_{50}$ value of 60 µg/cm$^2$ is obtained. Indomethacin, the reference drug, at the dose of 90 µg/cm$^2$ inhibits the oedematous response by almost 50%; from past data we can confirm that this dose of indomethacin represents its $ID_{50}$ value.

From the comparison between the $ID_{50}$ values of the tested substances, it can be stated the Asialene and L-Asialene possess pactically the same potency, that appears to be 50% higher than that of the reference drug, at least in this experimental model.

What is claimed is:

1. Salts of asiatic and madecassic acids with pharmaceutically acceptable organic bases, characterized in that said bases are selected from the group consisting of ethylenediamine, ethanolamine, diethanolamine, lysine, benzyltrimethylammonium hydroxide and tetramethylammonium hydroxide.

2. Salts of the asiatic and madecassic acids as claimed in claim 1 characterized in that they are in gel form consisting of said salts and water with a ratio between salt and water ranging from 1:12 to 1:20.

3. Pharmaceutical and cosmetic compositions suitable for topic and systemic treatment of erithema, varicose ulcers, venous insufficiency, bedsores, delayed cicatrization, ambustions, traumatic and surgery wounds, ophthalmic alloeosises, alloeosises of the cutaneous trophism and inflammatory diseases, comprising a pharmaceutically effective or cosmetically idoneous amount of a salt as claimed in claim 1 in mixture with a pharmaceutically acceptable or cosmetically idoneous excipient and/or diluent substances.

4. Process for the preparation of salts of asiatic or madecassic acid with pharmaceutically acceptable organic bases as claimed in claim 1, wherein:
   a) a solution of said organic base in an organic solvent is prepared;
   b) a solution of asiatic or madecassic acid in an organic solvent is prepared;
   c) the solution of asiatic or madecassic acid is added to the solution of the organic base;

d) the mixture obtained in the step c) is heated at a temperature ranging from 40 to 70° C.;

e) the solvent is removed and the residue is washed with an organic solvent and crystallized from organic solvent.

5. Process as claimed in claim 4, characterized in that the molar ratio between organic base and asiatic or madecassic acid ranges form 3:1 to 1:1.

6. A method of treating an inflammatory or wound-related disease, disorder or condition comprising: administering to an individual in need thereof an effective amount of salts of asiatic and madecassic acids with pharmaceutically acceptable organic bases, wherein the bases are selected from the group consisting of ethylenediamine, ethanolamine, diethanolamine, lysine, benzyltrimethylammonium hydroxide and tetramethylammonium hydroxide, thereby treating the inflammatory or wound-related disease, disorder or condition.

7. The method of claim 6, wherein the inflammatory or wound-related disease, disorder or condition is selected from the group consisting of erithema, varicose ulcers, venous insufficiency, bedsores, delayed cicatrization, ambustions, traumatic and surgery wounds, ophthalmic alloeosises, and alloeosises of the cutaneous trophism.

8. The method of claim 6, wherein the salts of asiatic and madecassic acids are in gel form consisting of said salts and water with a ratio between salt and water ranging from 1:12 to 1:20.

* * * * *